(12) United States Patent
Magee et al.

(10) Patent No.: US 11,806,243 B2
(45) Date of Patent: Nov. 7, 2023

(54) CEMENT PACKING KYPHOPLASTY SURGICAL DEVICE AND METHOD

(71) Applicant: FOCUS MEDICAL COMPANY, LLC, Edmond, OK (US)

(72) Inventors: Calvin Magee, Edmond, OK (US); Austin Head, Edmond, OK (US)

(*) Notice: Subject to any disclaimer, the term of this patent is extended or adjusted under 35 U.S.C. 154(b) by 0 days.

(21) Appl. No.: 17/963,260

(22) Filed: Oct. 11, 2022

(65) Prior Publication Data

US 2023/0037079 A1 Feb. 2, 2023

Related U.S. Application Data

(63) Continuation-in-part of application No. 17/690,457, filed on Mar. 9, 2022, which is a continuation-in-part of application No. 17/384,702, filed on Jul. 23, 2021, now Pat. No. 11,298,238.

(51) Int. Cl.
| | | |
|---|---|---|
| *A61F 2/44* | (2006.01) |
| *A61F 2/46* | (2006.01) |
| *A61B 17/88* | (2006.01) |
| *A61B 17/12* | (2006.01) |
| *A61B 17/70* | (2006.01) |
| *A61F 2/30* | (2006.01) |
| *A61B 17/00* | (2006.01) |

(52) U.S. Cl.
CPC ........ *A61F 2/441* (2013.01); *A61B 17/12186* (2013.01); *A61B 17/7097* (2013.01); *A61B 17/8855* (2013.01); *A61F 2/4611* (2013.01); *A61B 2017/00557* (2013.01); *A61F 2002/30224* (2013.01); *A61F 2002/30242* (2013.01); *A61F 2002/30263* (2013.01); *A61F 2002/4631* (2013.01)

(58) Field of Classification Search
CPC ............ A61B 17/7097; A61B 17/8852; A61B 17/8855; A61B 17/12186; A61F 2/44–447; A61F 2002/4415–4495
USPC .............................. 623/17.11–17.16
See application file for complete search history.

(56) References Cited

U.S. PATENT DOCUMENTS

| 6,140,452 | A | * | 10/2000 | Felt ........................ C08G 18/69 |
|---|---|---|---|---|
| | | | | 528/65 |
| 7,951,111 | B2 | | 5/2011 | Drasler et al. |
| 8,900,304 | B1 | | 12/2014 | Alobaid |
| (Continued) | | | | |

Primary Examiner — Matthew J Lawson
(74) Attorney, Agent, or Firm — Hollowell Patent Group; Kelly Hollowell (57) ABSTRACT

Apparatus and associated methods relate to a balloon kyphoplasty surgical device comprising an extrusion tube having internal fluid channels and a support wire, a port arrangement positioned on a proximal end of the extrusion tube and a balloon arrangement positioned on a distal end of the extrusion tube, the balloon arrangement resulting in a cubic shape when inflated by the port arrangement. An exemplary implementation may be configured with multiple inner balloons housed in an outer balloon to create a specific shape. Some designs may be configured with multiple ports designed to individually and independently inflate each inner balloon and outer balloon. The outer balloon may be inflatable. The outer balloon may be sealed off, constraining inflation of the inner balloons to create a cubic-like shape when the inner balloons are inflated within the sealed outer balloon, resulting in improved vertebral structure stabilization by increased surface area lifting the bone.

18 Claims, 8 Drawing Sheets

(56) References Cited

U.S. PATENT DOCUMENTS

| | | | |
|---|---|---|---|
| 9,168,072 B2 | 10/2015 | Singhatat et al. | |
| 10,111,689 B2 | 10/2018 | Rabiner et al. | |
| 10,426,453 B2 | 10/2019 | Kaiser et al. | |
| 10,799,348 B2 | 10/2020 | Tilson et al. | |
| 10,820,933 B1* | 11/2020 | Murdoch | A61G 13/121 |
| 11,103,290 B1* | 8/2021 | Murdoch | A61B 17/8855 |
| 11,103,902 B2* | 8/2021 | Banholzer | B65H 75/364 |
| 11,298,238 B1* | 4/2022 | Magee | A61F 2/4611 |
| 2005/0090901 A1* | 4/2005 | Studer | A61F 2/4611 |
| | | | 623/17.12 |
| 2005/0131267 A1* | 6/2005 | Talmadge | A61M 25/1002 |
| | | | 600/3 |
| 2005/0209674 A1 | 9/2005 | Kutscher et al. | |
| 2006/0100706 A1* | 5/2006 | Shadduck | A61B 17/7098 |
| | | | 623/17.11 |
| 2006/0106461 A1* | 5/2006 | Embry | A61B 17/7097 |
| | | | 623/17.12 |
| 2006/0182780 A1* | 8/2006 | Riley | A61B 17/7097 |
| | | | 604/99.01 |
| 2007/0055201 A1* | 3/2007 | Seto | A61B 17/1671 |
| | | | 604/96.01 |
| 2007/0055276 A1* | 3/2007 | Edidin | A61B 17/8855 |
| | | | 606/92 |
| 2007/0093899 A1* | 4/2007 | Dutoit | A61B 17/7097 |
| | | | 623/17.11 |
| 2011/0137317 A1* | 6/2011 | O'Halloran | A61B 17/7097 |
| | | | 606/92 |
| 2012/0010713 A1* | 1/2012 | O'Halloran | A61B 17/7097 |
| | | | 623/17.12 |
| 2012/0265167 A1* | 10/2012 | Simonson | A61B 17/7095 |
| | | | 604/506 |
| 2012/0277811 A1* | 11/2012 | Lauchner | A61B 17/56 |
| | | | 606/86 R |
| 2013/0218164 A1* | 8/2013 | Mueller | A61B 17/8858 |
| | | | 606/93 |
| 2014/0194885 A1* | 7/2014 | Lauchner | A61B 17/8811 |
| | | | 606/94 |
| 2016/0354130 A1* | 12/2016 | Auyoung | A61B 17/8805 |
| 2019/0365445 A1 | 12/2019 | Kallmes et al. | |
| 2020/0069391 A1 | 3/2020 | McEvaddy et al. | |

* cited by examiner

CEMENT PACKING KYPHOPLASTY SURGICAL DEVICE AND METHOD

CROSS-REFERENCE TO RELATED APPLICATIONS

This application is a Continuation-in-Part of U.S. patent application Ser. No. 17/690,457, filed Mar. 9, 2022, which is a Continuation-in-Part of U.S. patent application Ser. No. 17/384,702, filed Jul. 23, 2021, now U.S. Pat. No. 11,298,238, and the entire contents of all of the above-referenced applications are incorporated herein by reference.

BACKGROUND

The present invention relates generally to medical devices, and more specifically to a balloon kyphoplasty surgical device.

In general, balloon kyphoplasty is a modified vertebroplasty technique. It is a minimally invasive procedure that aims to relieve pain, restore vertebral height, and correct kyphosis. During this procedure, an inflatable bone tamp is inserted into the collapsed vertebral body. Once inflated, the balloon elevates the end plates creating lift and thereby restores the height of the vertebral body. The balloon moves or shifts the pieces of broken or compressed vertebral bone and forms a space, i.e., a bony void when it is inflated. The balloon is deflated and removed, and the bony void is filled with bone cement.

The following presents a simplified summary of the innovation in order to provide a basic understanding of some aspects of the present disclosure. This summary is not an extensive overview of the present disclosure. It is intended to neither identify key or critical elements of the present disclosure nor delineate the scope of the present disclosure. Its sole purpose is to present some concepts of the present disclosure in a simplified form as a prelude to the more detailed description that is presented later.

SUMMARY

In an aspect, an exemplary implementation in accordance with the present disclosure may feature a balloon kyphoplasty surgical device including an extrusion tube having internal fluid channels and a support wire, a port arrangement positioned on a proximal end of the extrusion tube and a balloon arrangement positioned on a distal end of the extrusion tube, the balloon arrangement resulting in a predetermined shape when inflated by the port arrangement. In an example illustrative of various implementations in accordance with the present disclosure, the inflated balloon arrangement's predetermined shape may be a cubic, rectangular, or prism shape, or another shape.

In another aspect, an exemplary implementation in accordance with the present disclosure may feature a kyphoplasty balloon arrangement including inner balloons, and an outer balloon, the inner balloons being housed within the outer balloon.

In still another aspect, an exemplary implementation in accordance with the present disclosure may feature a kyphoplasty surgical method including placing a patient face down on a table, cleaning the patient's back, administering a local anesthesia, making a small incision in the patient's back, placing an extrusion tube through the incision, pushing the extrusion tube along a path through a pedicle of an involved vertebra and into a fractured area and inflating a balloon arrangement located on a distal end of the extrusion tube into a cubic shape.

In still another aspect, an exemplary implementation in accordance with the present disclosure may be configured with multiple inner balloons housed in an outer balloon to create a specific shape, using multiple ports configured to individually and independently inflate respective multiple inner balloons retained within a sealed off outer balloon to constrain and create a cubic-like (or square) shape when the inner balloons are inflated.

Some exemplary implementations in accordance with the present disclosure may achieve one or more advantage. These and other such advantages will be further understood and appreciated by those skilled in the art by reference to the following written specification, claims and appended drawings.

DETAILED DESCRIPTION

It is to be understood that the specific devices and processes illustrated in the attached drawings and described in the following specification are exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
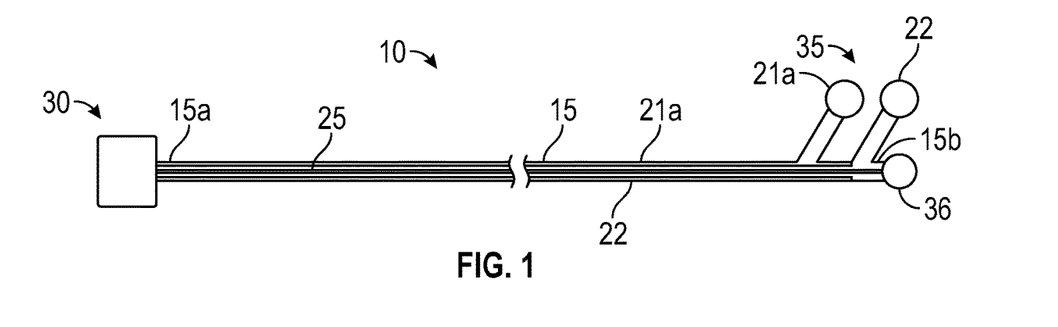
FIG. 1 depicts an exemplary balloon kyphoplasty surgical device configured with an inflatable outer balloon.
Figure 3:
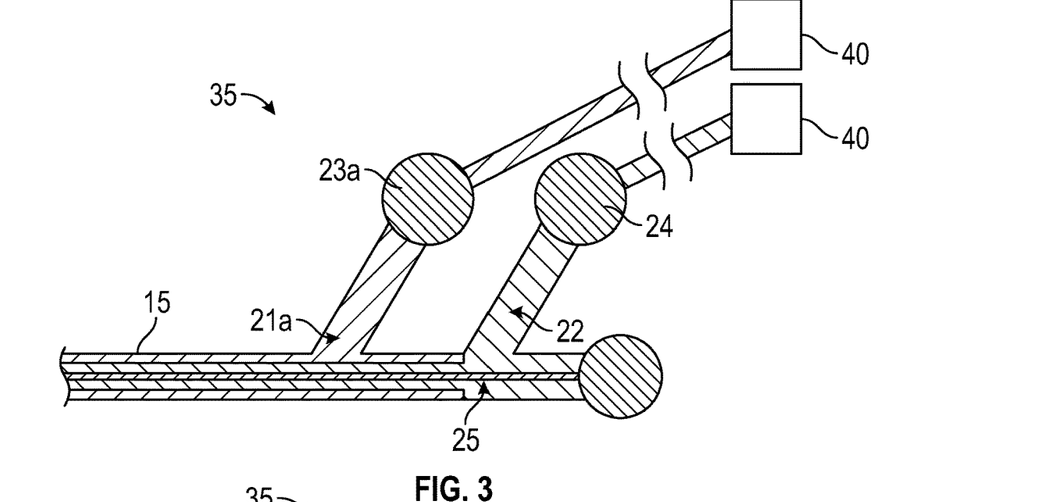
FIG. 3 is an enlarged cutaway side view of an exemplary port arrangement.
Figure 4:
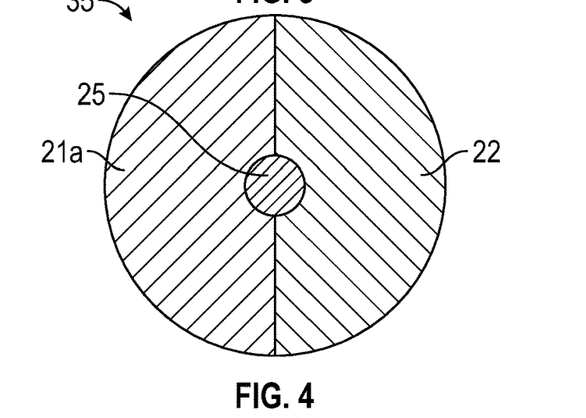
FIG. 4 is a side cross sectional view of an exemplary dual port/channel configuration of the port arrangement with one port/channel for the four inner balloons and one port/channel for the outer balloon.
Figure 5:
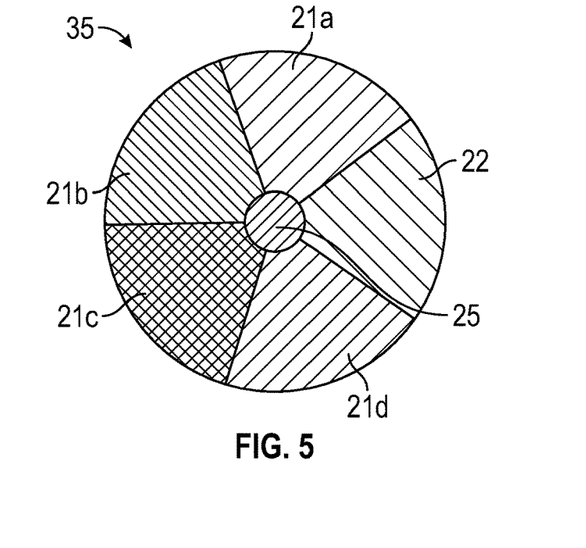
FIG. 5 is a side cross sectional view of an exemplary multi-port/channel configuration of the port arrangement having 5 port/channels with one port/channel for each of the four inner balloons and one port/channel for an outer balloon.

As shown in FIG. 1, the exemplary balloon kyphoplasty surgical device 10 includes the extrusion tube 15 having at least two internal fluid channels 21a, 22. Although only two internal channels 21a, 22 are illustrated in FIGS. 1, 3 and 4, it should be appreciated that additional channels may be contained within the extrusion tube 15 as illustrated in FIG. 5. In one embodiment, the extrusion tube 15 includes five internal fluid channels described in more detail below. Housed within a length of the extrusion tube 15 is a support wire 25. Positioned on a distal end 15a of the extrusion tube 15 is a balloon arrangement 30 in fluid communication with the at least two fluid channels 21a, 22. Positioned on a proximal end 15b of the extrusion tube 15 is a port arrangement 35 in fluid communication with the at least two fluid channels 21a, 22 and a termination cap 36.

With the balloon kyphoplasty surgical device 10 implementation depicted by FIG. 1, when the balloon arrangement 30 is inflated, the balloon arrangement 30 lifts with a predetermined shape resulting from the shapes of individual balloons comprising the balloon arrangement 30. In an example illustrative of various implementations in accordance with the present disclosure, the balloon arrangement 30 may comprise a plurality of individual balloons. The plurality of individual balloons may comprise an outer balloon. The outer balloon may be inflatable. The outer balloon may be manufactured to be an uninflatable outer balloon. The outer balloon may be sealed. For example, an uninflatable outer balloon may be manufactured as a sealed outer balloon. The outer balloon may be sealed during assembly or use of an exemplary balloon kyphoplasty surgical device 10. Exemplary design, operation, and usage of a balloon kyphoplasty surgical device 10 implementation configured with a sealed outer balloon are described at least with reference to FIG. 9. The outer balloon may be manufactured to have a predetermined shape. The outer balloon may be manufactured to retain the predetermined outer balloon shape when the outer balloon is inflated. The outer balloon may retain one or more inner balloon. The one or more inner balloon may be inflatable. The one or more inner balloon may be manufactured to have a predetermined shape. The inner balloon may be manufactured to retain the predetermined inner balloon shape when the inner balloon is inflated. The outer balloon may be substantially cube-shaped. The outer balloon may be substantially cylindrical. The outer balloon bay be substantially spherical. The one or more inner balloon may be substantially spherical. The one or more inner balloon may be substantially cylindrical. The one or more inner balloon may be substantially cube shaped. The one or more inner balloon may be substantially pyramid-shaped. The one or more inner balloon may be substantially oval. The one or more inner balloon may be substantially elliptical. The one or more inner balloon may further comprise a plurality of inner balloons. One or more inner balloon of the plurality of inner balloons may have a shape different from another inner balloon of the plurality of inner balloons. The plurality of inner balloons may comprise inner balloons having a plurality of different shapes. The plurality of inner balloons may comprise inner balloons having a plurality of different sizes. The balloon arrangement may be inflated. A balloon arrangement's outer balloon may be inflated to a volume or pressure different from one or more inner balloon's volume or pressure. One or more inner balloon of a balloon arrangement's plurality of inner balloons may be inflated to a volume or pressure different from one or more other inner balloon's volume or pressure. The balloon arrangement may have a cubic or cubic-type shape, rather than a circular-type shape, as is found in prior kyphoplasty devices.

Figure 2A:
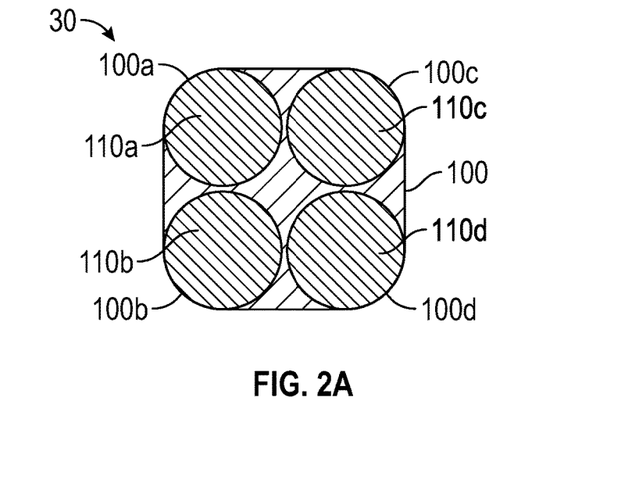
FIGS. 2A-2F depict various top cross-section cutaway views of exemplary balloon arrangements.
Figure 2B:
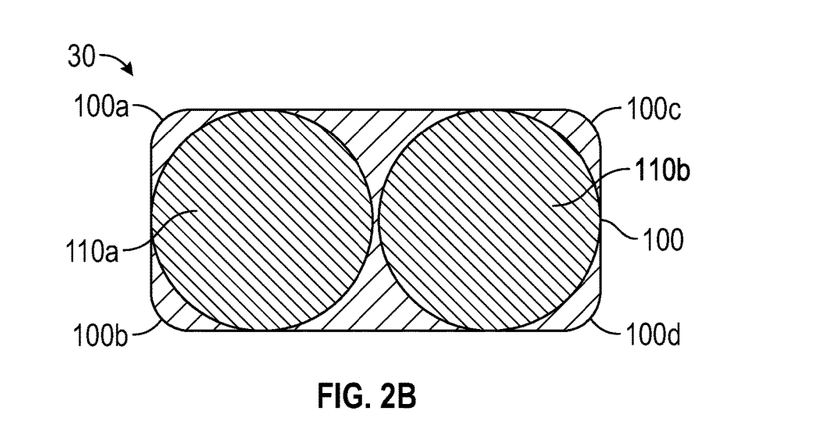
Figure 2C:
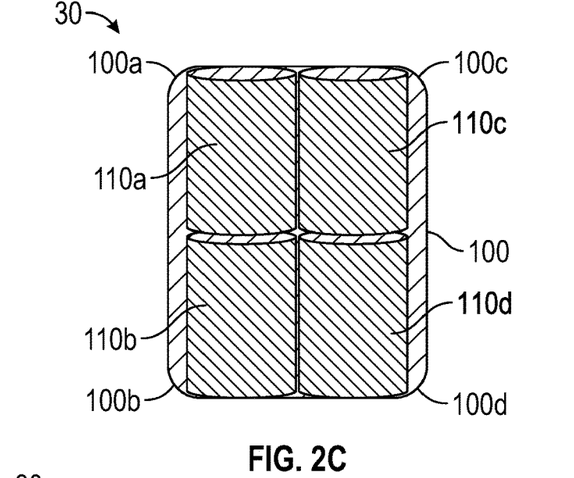
Figure 2D:
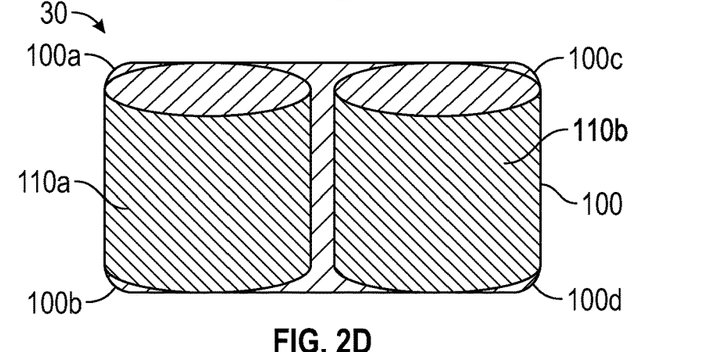
Figure 2E:
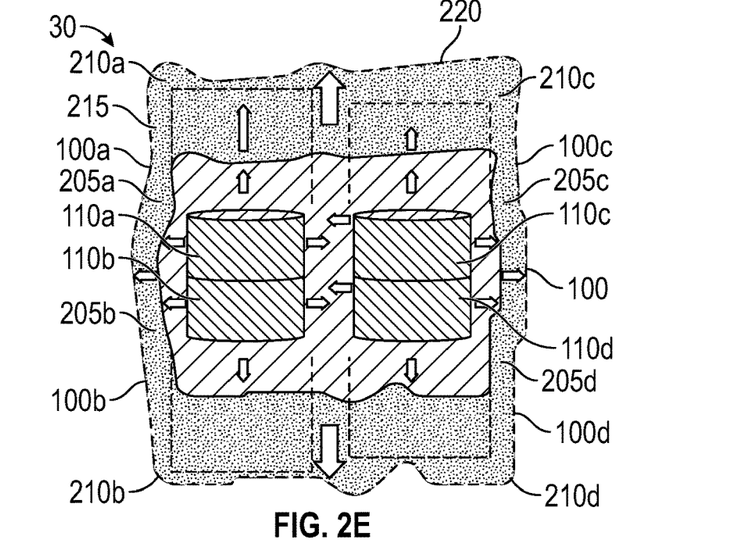
Figure 2F:
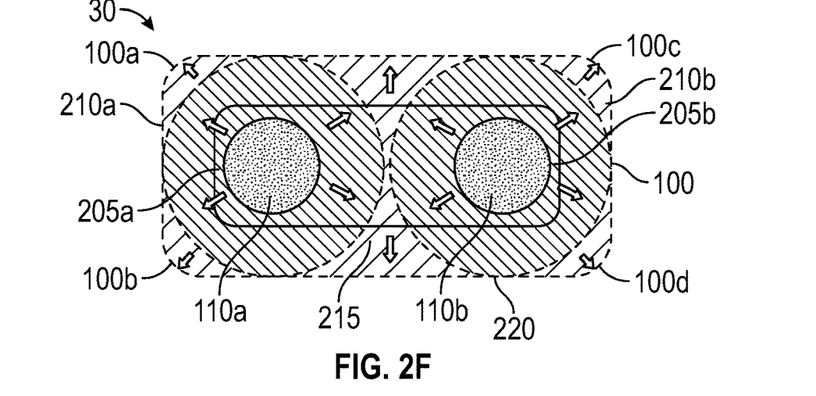
Figure 2G:
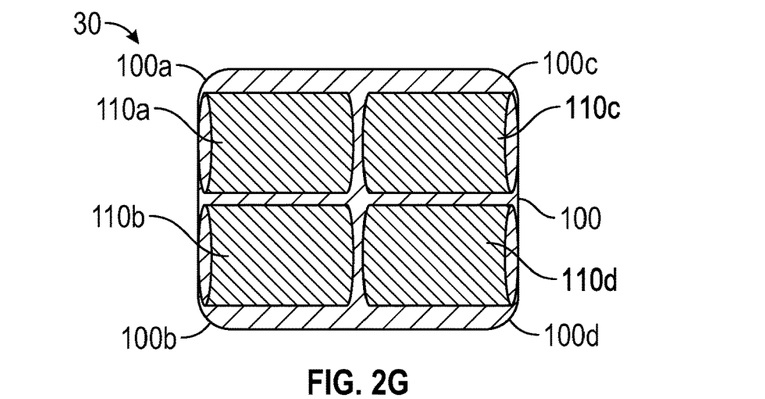
FIGS. 2G-2I depict front perspective cutaway views of exemplary balloon arrangements.

Referring now to FIG. 2A, a top cross-section cutaway view of the inflated balloon arrangement 30 is shown that enables the balloon arrangement 30 to form a cubic-type shape. Here, the balloon arrangement 30 includes an outer balloon 100 that houses four inner balloons 110a, 110b, 110c, and 110d. The outer balloon 100 may be inflatable. The outer balloon may be sealed. The sealed outer balloon may be manufactured to be uninflatable. In the implementations depicted by FIGS. 2A-2I the outer balloon 100 is an inflatable outer balloon. An exemplary balloon kyphoplasty surgical device 10 implementation configured with a sealed outer balloon is further described at least with reference to FIG. 9. In the depicted balloon arrangement 30 implementation, the outer balloon 100 has been manufactured to be cubic in shape, while the inner balloons 110a, 110b, 110c, and 110d have been manufactured to have a cylindrical and/or spherical shape and support the corners 100a,b,c,d of the outer balloon 100 to maintain a cubic geometry of the inflated balloon arrangement 30 under pressure. The depicted cubic-shaped outer balloon 100 comprises eight corners. In the balloon arrangement 30 top view depicted by FIG. 2A, the outer balloon 100 corners 100e,f,g,h are not visible. Exemplary outer balloon 100 corners 100e,f,g,h are shown with the corners 100a,b,c,d in FIG. 2H. In another embodiment, various other geometric shapes of inner balloons and/or varying numbers of inner balloons may be combined to create the cubic shape of the kyphoplasty surgical device. For example, an exemplary kyphoplasty surgical device balloon arrangement implementation may be configured with two inner spherical balloons and one outer balloon as shown, for example, in FIG. 2B. In FIG. 2B, the outer balloon 100 retains two inflated spherical inner balloons, 110a and 110b. Another exemplary kyphoplasty surgical device balloon arrangement implementation may be configured with four inner cylindrical balloons and one outer balloon as shown, for example, in FIG. 2C, illustrating the four inflated cylindrical inner balloons 110a, 110b, 110c, and 110d. Another exemplary kyphoplasty surgical device balloon arrangement implementation may be configured with two inflated inner cylindrical balloons 110a and 110b and one outer balloon 100 as shown, for example, in FIG. 2D. Some balloon arrangement implementations in accordance with the present disclosure may include an inner balloon configured to be independently inflated to a pressure or volume different from other balloons in the balloon arrangement 30. In the balloon arrangement 30 implementation depicted by FIG. 2E, the four uninflated cylindrical inner balloons 110a, 110b, 110c, 110d are independently and separately inflated. The cylindrical inner balloons 110a, 110b, 110c, 110d expand when inflated from respective uninflated volumes 205a,b,c,d to respective inflated volumes 210a,b,c,d, and the outer balloon 100 expands when inflated from the uninflated volume 215 to the inflated volume 220. In the balloon arrangement 30 implementation depicted by FIG. 2F, the two uninflated spherical inner balloons 110a and 110b are independently and separately inflated. The spherical inner balloons 110a and 110b expand when inflated from respective uninflated volumes 205a,b to respective inflated volumes 210a,b, and the outer balloon 100 expands from the uninflated volume 215 to the inflated volume 220. In an illustrative example, a kyphoplasty surgical device balloon arrangement implementation in accordance with the present disclosure may comprise a variety of diverse balloon shapes and/or sizes. An exemplary kyphoplasty surgical device balloon arrangement implementation in accordance with the present disclosure may comprise any number of inner balloons. One or more cylindrical inner balloon of a kyphoplasty surgical device balloon arrangement implementation may be disposed with the one or more inner balloon's longitudinal axis substantially parallel with the longitudinal axis of a patient's spine when the kyphoplasty surgical device is inserted into a collapsed vertebral body. One or more cylindrical inner balloon of a kyphoplasty surgical device balloon arrangement implementation may be disposed with the one or more cylindrical inner balloon's longitudinal axis substantially perpendicular with the longitudinal axis of a patient's spine when the kyphoplasty surgical device is inserted into a collapsed vertebral body, as depicted, for example, by FIG. 2G in a front view. In the example depicted by FIG. 2G, the four inflated cylindrical inner balloons 110a, 110b, 110c, and 110d are disposed with their respective longitudinal axes perpendicular with a viewer's line of sight into the drawing sheet. In some balloon arrangement 30 implementations, a mix of balloon shapes may be configured to provide a customized contour improving the effective support of involved vertebrae. Inner balloons may be inflated to different pressures, to improve lift at different points on surfaces of involved vertebral bodies, to enhance the effectiveness of installation and improve the chance of a positive patient outcome. For example, a spherical balloon may be configured close to a cylindrical balloon, to provide support customized to an uneven surface of an involved vertebral body. Although FIG. 2G depicts a front view illustrating a plurality of cylindrical inner balloons of a kyphoplasty surgical device balloon arrangement 30 implementation disposed with the inner balloon's longitudinal axes substantially perpendicular with the longitudinal axis of a patient's spine, other orientations of the cylindrical balloons are possible. For example, an exemplary implementation may include one or more cylindrical inner balloon disposed in any orientation useful to improve treatment effect. For example, an exemplary cylindrical balloon may have two substantially parallel circular bases joined at a fixed distance by a curved surface. In an exemplary implementation, a cylindrical inner balloon may be oriented within an outer balloon to align at least one cylindrical inner balloon's base with an outer balloon's inner edge. In an illustrative example using the kyphoplasty surgical device balloon arrangement 30 implementation depicted by FIG. 2G in a front view, if the cylindrical inner balloons 110a, 110b, 110c, and 110d were rotated to align a base of each cylindrical inner balloon 110a, 110b, 110c, and 110d with the outer balloon's top inner edge, the cylindrical inner balloons 110a, 110b, 110c, and 110d respective top bases would appear in a top view as four circles, as depicted by FIG. 2A. Aligning at least one cylindrical inner balloon's base with an outer balloon's inner edge may reduce the force per unit area supported by the cylindrical inner balloon, as a result of increased surface area engaged in load support. In an illustrative example, reducing the force per unit area supported by an inner balloon may help reduce the cost of kyphoplasty surgical device implementation by permitting the use of less expensive balloon material. In some implementations, reducing the force per unit area supported by an inner balloon may improve the effectiveness of stabilizing a collapsed vertebral body. Such improved vertebral body stabilization effectiveness may be a result of stabilization force from balloon inflation that is more evenly distributed over an increased area.

In an illustrative usage scenario of an exemplary kyphoplasty surgical device balloon arrangement 30 implementation configured with four balloons, after insertion into the fractured area, the inner balloons 110a, 110b, 110c, and 110d, and the outer balloon 100 are inflated. More specifically, the inner balloons 110a, 110b, 110c, and 110d are inflated to a size needed for the appropriate distance of lift, while the outer balloon 100 is inflated to have a volume of fluid added that is equal to the remaining volume needed to produce a cubic shape having 4 corners 100a,b,c,d for the inflated balloon arrangement 30. Inflation of the inner balloons 110a, 110b, 110c, and 110d and the outer balloon 100 is accomplished by the port arrangement 35.

Figure 2H:
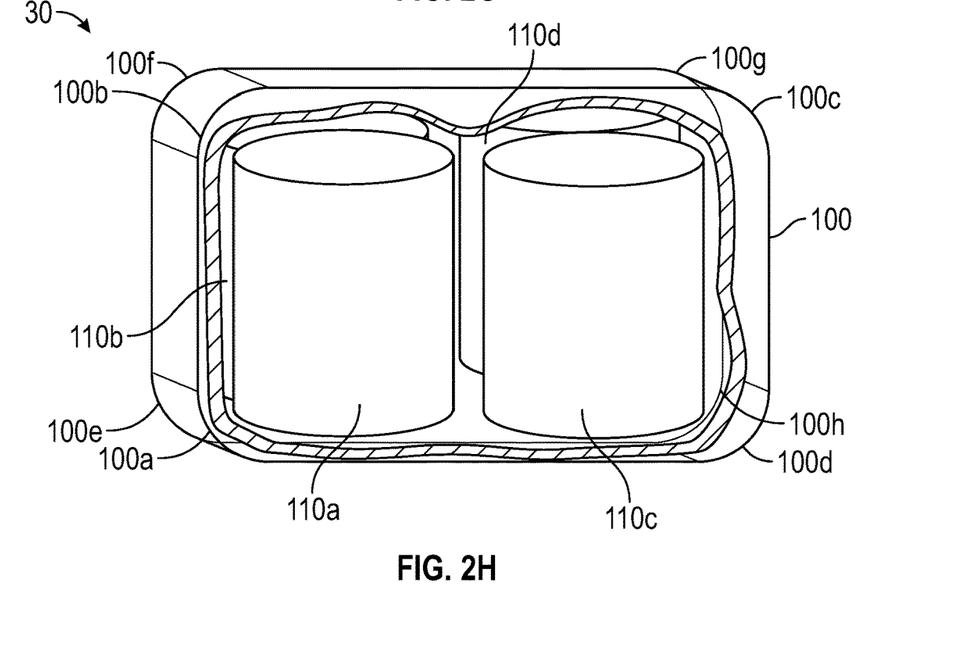
Figure 2I:
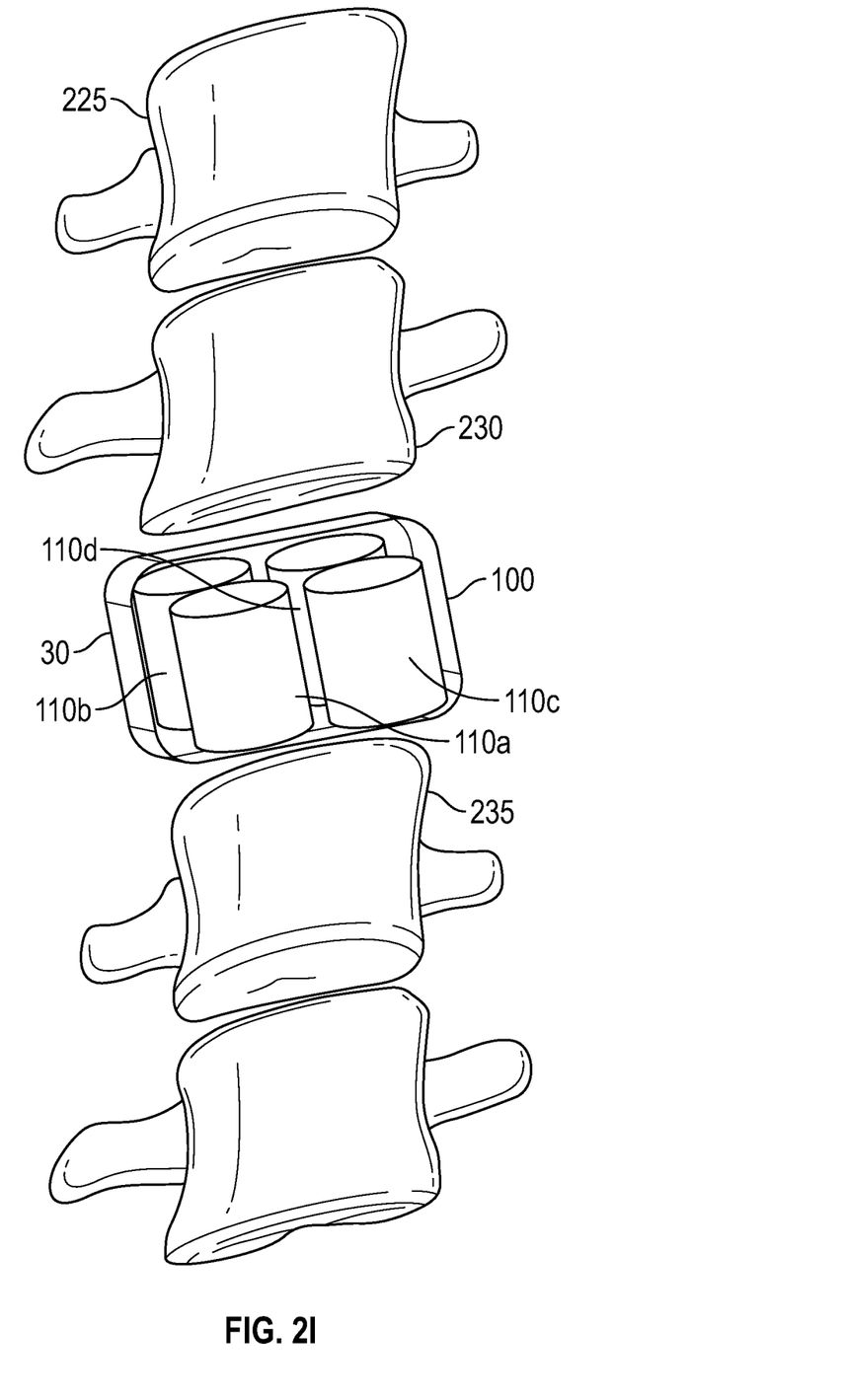

In the exemplary balloon arrangement 30 implementation depicted by FIG. 2H in a front perspective cutaway view, the exemplary outer balloon 100 eight corners 100a,b,c,d,e,f,g are visible, defining a cubic-type outer balloon 100 shape. The balloon arrangement 30 implementation depicted by FIG. 2H is shown for illustration purposes in a cutaway view to permit viewing the inflated inner balloons 110a, 110b, 110c, and 110d retained within the outer balloon 100. In FIG. 2I, the exemplary balloon arrangement 30 implementation is depicted with a portion of the human spine 225. In the illustrated example, the balloon arrangement 30 is positioned to lift or support the upper involved vertebra 230 and the lower involved vertebra 235. The depicted balloon arrangement 30 includes the inflated inner cylindrical balloons 110a, 110b, 110c, and 110d. In the depicted example, the inner balloon 110d is visible in perspective just behind the outer balloon 110c.

In one embodiment and as shown in FIG. 3, the port arrangement 35 includes two ports 23a, 24 linked to respective chambers 21a, 22 (referred to interchangeably as channels or passages). In one embodiment, incompressible fluid will be used to inflate the balloons such as but not limited to contrast fluid, contrast liquid and contrast fluid for Xray depiction. The two ports 23a, 24 are not only linked to but also in fluid communication with the respective chambers 21a, 22. Together, the ports and chambers are referred to as port/channels. The ports 23a and 24 are also in fluid communication with inflation device reservoirs 40. The inflation device reservoirs 40 are themselves controlled by a standard fluid pressure mechanism such as but not limited to valves working in concert with fluid pressure gauges and a balloon inflation device (which uses fluid) (not shown). In the depicted implementation, the inflation device reservoirs 40 retain contrast fluid.

FIG. 4 illustrates a side cross sectional view of a dual port/channel configuration of the port arrangement with one port/channel for the four inner balloons and one port/channel for the outer balloon.

In one embodiment and as illustrated in FIG. 5, the port arrangement 35 includes one port/channel for each of the four inner balloons and one port/channel for an outer balloon (ports not shown). FIG. 5 is a side cross sectional view of a multi-port/channel configuration of the port arrangement having 4 port/channels with one port/channel for each of the four inner balloons and one port/channel for an outer balloon. The presence of multiple ports/channels within the extrusion tube 15 enables at least one inflation device reservoir 40 controlled by standard fluid pressure gauges and valve mechanisms (not shown) to maintain the pressure and volume used to inflate the respective inner and outer balloons that make up the balloon arrangement 30. In one embodiment, there are at least two inflation device reservoirs 40 that independently maintain the pressure and volume used to inflate the respective inner and outer balloons that make up the balloon arrangement 30.

Figure 6:
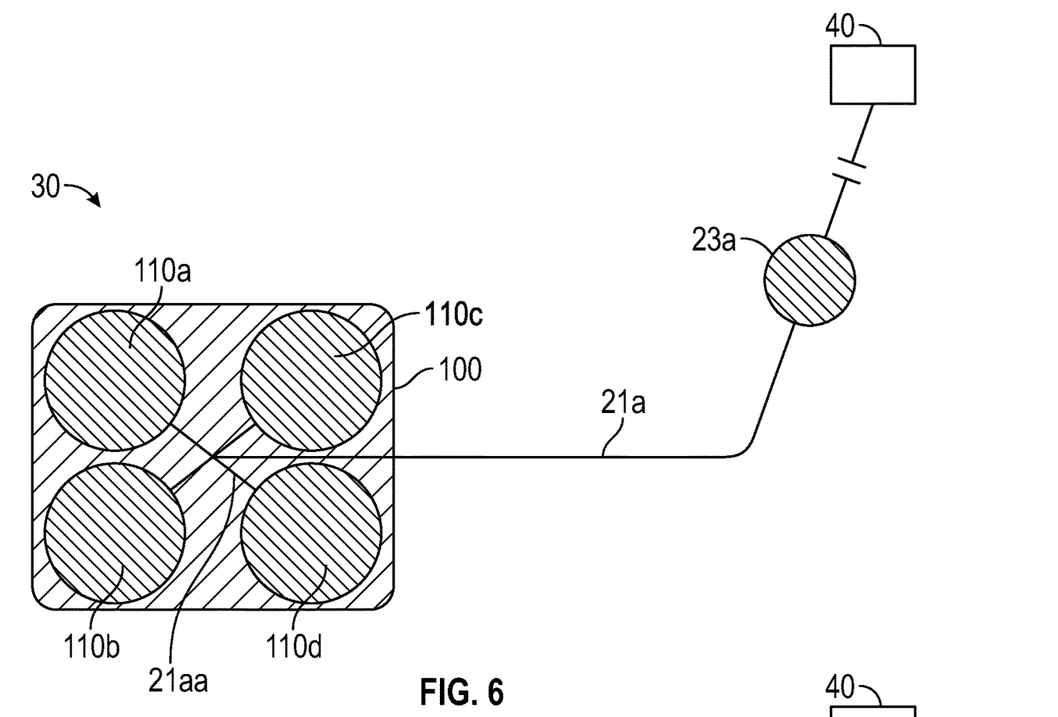
FIG. 6 is a top cross-sectional view and schematic of an exemplary single port/channel terminating in four airway branches in fluid connection with the four inner balloons.

FIG. 6 is a top cross-sectional view and schematic of a single port/channel terminating in four airway branches 21aa in fluid connection with the four inner balloons. In the implementation depicted by FIG. 6, the four airway branches 21aa are four branches of the chamber 21a into respective inner balloons.

Figure 7:
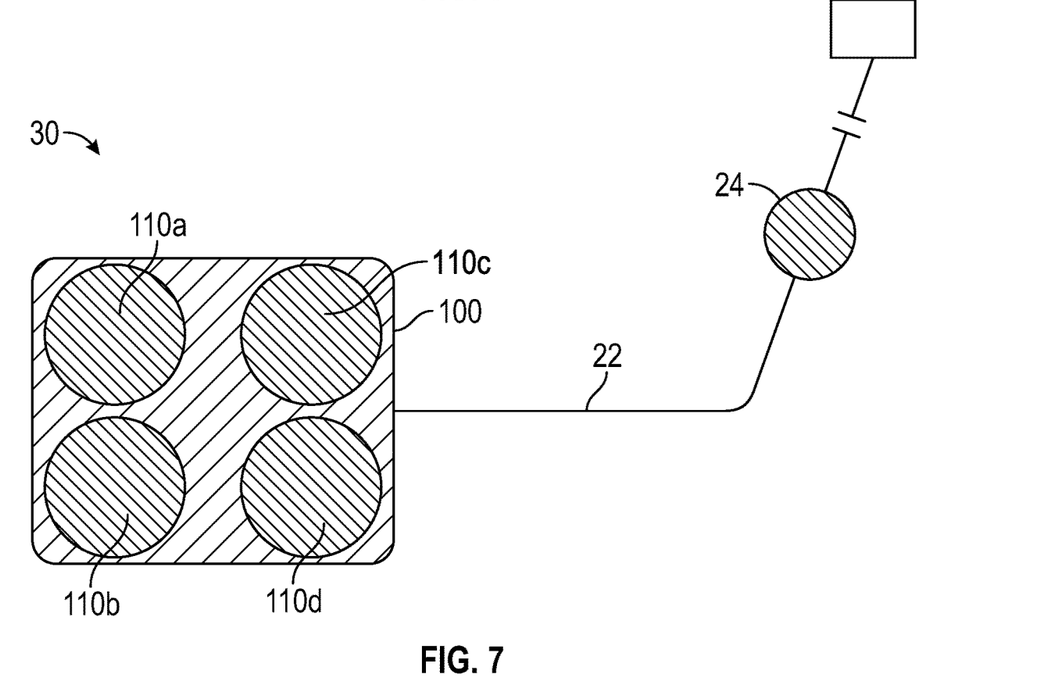
FIG. 7 is a top cross-sectional view and schematic of an exemplary single port/channel terminating in fluid connection with the outer balloon.

FIG. 7 is a top cross-sectional view and schematic of a single port/channel terminating in fluid connection with the outer balloon.

Figure 8:
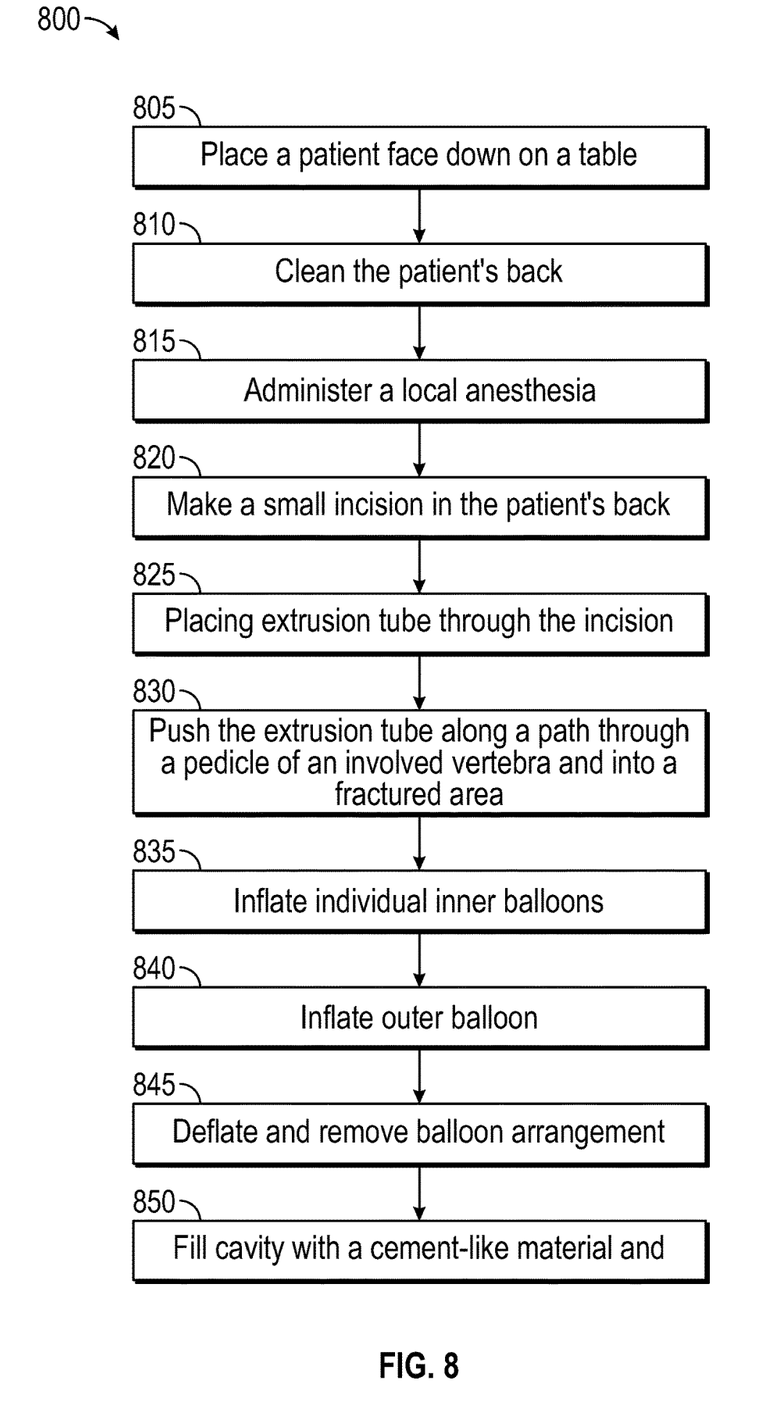
FIG. 8 is a flow diagram of an exemplary kyphoplasty surgical process.

FIG. 8 is a flow diagram of an exemplary kyphoplasty surgical process. As shown in FIG. 8, an exemplary kyphoplasty surgical process 800 includes placing (805) a patient face down on a table.

The kyphoplasty surgical process 800 includes cleaning (810) the patient's back and administering (815) a local anesthesia.

The kyphoplasty surgical process 800 includes making (820) a small incision in the patient's back and placing (825) an exemplary kyphoplasty surgical device extrusion tube through the incision. The method may include positioning an exemplary kyphoplasty surgical device to ensure a balloon is aligned to be square with the vertebra so the flat surface is parallel to the vertebra.

The kyphoplasty surgical process 800 includes pushing (830) the extrusion tube along a path through a pedicle of an involved vertebra and into a fractured area.

Once in the fractured area, inner balloons retained within an outer balloon of a balloon arrangement are inflated (835). The inner balloons may be spherically shaped. The inner balloons may be cylindrically shaped. The outer balloon may be cubic shaped.

Once the inner balloons are inflated, the outer balloon in the balloon arrangement is inflated (840), resulting in the balloon arrangement having a cubic shape, lifting the target area such as a vertebrae or fracture.

The balloon arrangement is then deflated and removed (845), and the cavity is gradually filled (850) with a cement-like material and allowed to harden.

Figure 9:
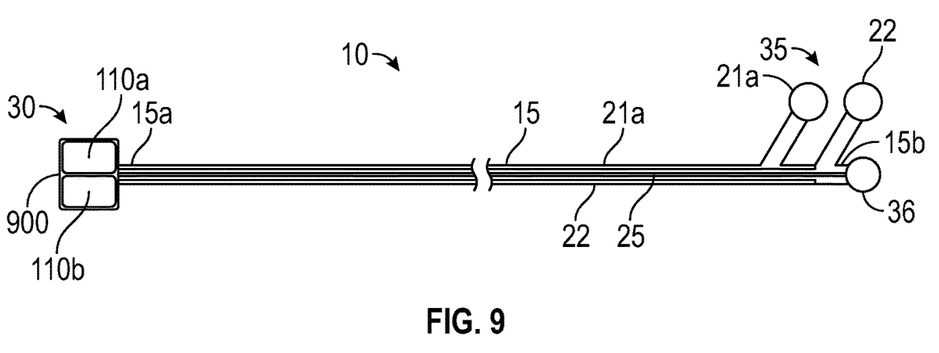
FIG. 9 depicts an exemplary balloon kyphoplasty surgical device configured with a sealed outer balloon.

FIG. 9 depicts an exemplary balloon kyphoplasty surgical device configured with a sealed outer balloon. In FIG. 9, the exemplary balloon kyphoplasty surgical device 10 includes the extrusion tube 15 having at least two internal fluid channels 21a, 22. Although only two internal channels 21a, 22 are illustrated in FIGS. 1, 3, 4 and 9, it should be appreciated that additional channels may be contained within the extrusion tube 15 as described with reference to FIG. 5. In one embodiment, the extrusion tube 15 includes five internal fluid channels. Housed within a length of the extrusion tube 15 is a support wire 25. Positioned on a distal end 15a of the extrusion tube 15 is a balloon arrangement 30 in fluid communication with the at least two fluid channels 21a, 22. Positioned on a proximal end 15b of the extrusion tube 15 is a port arrangement 35 in fluid communication with the at least two fluid channels 21a, 22 and a termination cap 36.

In the exemplary balloon kyphoplasty surgical device 10 implementation depicted by FIG. 9, the balloon arrangement 30 comprises the inflatable inner balloons 110a and 110b, and the sealed outer balloon 900. The exemplary inner balloons 110a and 110b depicted by FIG. 9 may comprise any of the inner balloon features described herein at least with reference to FIGS. 1, 2A-2I, and 3-8.

With the balloon kyphoplasty surgical device 10 implementation depicted by FIG. 9, when the balloon arrangement 30 is inflated, the inflatable inner balloons 110a and 110b inflate within the sealed outer balloon 900. In the illustrated implementation, the sealed outer balloon 900 constrains the expansion of the inflatable inner balloons 110a and 110b to create a more defined cubic-like shape when the inner balloons 110a and 110b are inflated. In an illustrative example the sealed outer balloon 900 may constrain the expansion of the inflatable inner balloons 110a and 110b with more force spread over a greater surface area than an inflatable outer balloon, improving the results of surgery and reducing a surgeon's effort stabilizing vertebral structures. For example, using the sealed outer balloon 900 inner surface to constrain the expansion of the inflatable inner balloons 110a and 110b may increase the contact surface area between the inner balloons 110a and 110b with the sealed outer balloon 900 inner surface. Increasing the contact surface area between the inner balloons 110a and 110b and the sealed outer balloon 900 inner surface may reduce the force per unit area supported by an inner balloon and more evenly distribute force from the vertebrae over an increased area of the inner balloon, permitting more effective stabilization of the vertebral bodies. Using the sealed outer balloon 900 inner surface to constrain the expansion of the inflatable inner balloons 110a and 110b may reduce a surgeon's effort adjusting the inflation of the inner balloons 110a and 110b to stabilize a collapsed vertebral body. When the inflatable inner balloons 110a and 110b inflate within the sealed outer balloon 900, the balloon arrangement 30 lifts with a cubic or cubic-type shape, in contrast with some prior kyphoplasty devices that may lift with a circular-type shape.

In illustrative examples, the balloon kyphoplasty surgical device 10 implementation depicted by FIG. 9 includes the sealed outer balloon 900 that may house two or more inner balloons. The sealed outer balloon 900 may be manufactured to conform to the shape of the two or more inner balloons. The inner balloons may be configured to have a cube shape to create the corners of the sealed outer balloon 900. Creating the corners of the sealed outer balloon 900 using the cube shapes of the inflatable inner balloons helps to maintain a cubic geometry of the inflated balloon arrangement 30 under pressure. In an implementation, various other geometric shapes may be combined to create the cubic shape of the exemplary balloon kyphoplasty surgical device 10, such as but not limited to using two cylinders. In an illustrative example, after insertion into the fractured area, the inner balloons 110a and 110b may be inflated within the sealed outer balloon 900. More specifically, the inner balloons 110a and 110b may be inflated to a size needed for the appropriate distance of lift, while the sealed outer balloon 900 conforms around the inner balloons 110a and 110b as they inflate, creating a square shape. The sealed outer balloon 900 may be configured without its own port. The sealed outer balloon 900 may be sealed during manufacturing. Inflation of the inner balloons 110a and 110b and the conforming of the sealed outer balloon 900 may be accomplished by the inner balloons individual port arrangement 35. In the implementation depicted by FIG. 9, the port arrangement 35 includes two ports linked to respective chambers 21a, 22 (referred to interchangeably as channels, lumens or passages). The two ports are not only linked to but also in fluid communication with the respective chambers. Together, the ports and chambers are referred to as port/lumens (referred to interchangeably as port/channels). The ports are also in fluid communication with inflation device reservoirs, described herein at least with reference to FIGS. 3, 6 and 7. The inflation device reservoirs are themselves controlled by standard fluid pressure mechanisms such as but not limited to valve mechanisms. In an illustrative example, a technical effect of the inner balloons each having their own respective ports is to control the size each balloon is inflated to. For example, depending on the fracture, the balloons may need to be inflated at different heights to achieve the result needed, or one balloon may need more pressure to have equal height on both sides.

In illustrative example the exemplary balloon kyphoplasty surgical device 10 implementation depicted by FIG. 9 may be made up of multiple balloons, an extrusion tube, support wire, and a multichambered proximal port. The multiple balloons may be positioned as inner and outer balloons configured to produce a cubic shape when the inner balloons are inflated within the outer balloon. An exemplary balloon kyphoplasty surgical device 10 implementation may be configured with one or more larger outer balloons manufactured to conform and constrain the inner balloons. The one or more outer balloon may be sealed. The inner balloons may be made to have various shapes as would be known to one of ordinary skill in the art. For example one or more inner balloon may be made to have a cubic shape configured to support the corners of the sealed outer balloon and create a cubic like shape geometry of the balloon arrangement 30 under pressure. The extrusion tube 15 comprises multiple fluid channels so that the inner balloons can be inflated at different volumes or pressures and the outer balloon is sealed off. Sealing off the outer balloon may help limit the overall profile of the device enabling it to fit through the trocar. In an illustrative example the outer balloon may also constrain and help the inner balloons maintain their shape as well as create a cubic like shape once the inner balloons are inflated. The support wire 25 helps to prevent damage to the device while inserting into the vertebra. The multichambered proximal port may comprise multiple ports that attach to separate lumens. These lumens may connect to different fluid routes, keeping the inlets separate. Separation of the inlets will allow for independent filling during use.

In an illustrative example, a goal of using an exemplary balloon kyphoplasty surgical device 10 may be to achieve lift with a cubic-like balloon shape. Such lift from a cubic-like balloon shape may be a result of using a balloon kyphoplasty surgical device implementation using various components as described herein to achieve an exemplary cubic-like balloon shape. In an exemplary usage scenario for a balloon kyphoplasty surgical device, after insertion the inner balloons are inflated to the size needed for the appropriate distance of lift. The outer balloon will constrain the inner balloons and produce the cubic shape. The inner balloons are inflated using the multichambered ports and separate inflation device reservoirs to maintain the appropriate pressure/volume needed. The balloons may be made using material selected to be noncompliant enough to undergo a minimum of 400 PSI without losing the cubic shape or bursting while still being compliant enough to stretch to the appropriate size.

In an illustrative example, various prior art kyphoplasty balloons may use a standard circular balloon. The circular cavity created using a prior art circular balloon may cause problems including weakening bone and interfering with surgery by preventing adequate cement to be used during a procedure. For example the cement structure formed after use of a prior art kyphoplasty device using a circular balloon may have high single point pressure areas that can weaken the bone at these points. In addition a prior art kyphoplasty device using a circular balloon may also not allow for enough bone cement to be added for proper support.

In contrast with a prior art kyphoplasty device using a circular balloon, an exemplary balloon kyphoplasty surgical device 10 implementation designed and used in accordance with the teachings of the present disclosure is configured to create a larger boney void with a larger flat surface area producing a more structurally sound structure after cementation. In various implementations in accordance with the present disclosure, during compression of vertebra the bone is grown to exert this force through flat surfaces, and the cubic cement structure allows for a flat surface for the bone to compress on and for more cement to be packed in.

An exemplary balloon arrangement implementation in accordance with the present disclosure may create a larger cavity permitting more cement to be added, resulting in a more structurally sound structure after cementation. During compression of vertebra, the bone may be grown to exert this force through flat surfaces, and the cubic cement structure enables a flat surface for the bone to compress on and for more cement to be packed in.

An exemplary balloon kyphoplasty surgical device 10 implementation in accordance with the present disclosure may be configured with multiple inner balloons housed in an outer balloon to create a specific shape, use more than one port to inflate the inner balloons individually, and use a sealed off outer balloon to constrain and create a cubic-like (or square) shape when the inner balloons are inflated. In an illustrative example a balloon kyphoplasty surgical device 10 implementation in accordance with the present disclosure may use a cubic like shape to increase the surface area lifting the bone and may permit different orientations and fracture lifting techniques due to asymmetric shape of the balloons.

An exemplary balloon kyphoplasty surgical device 10 implementation in accordance with the present disclosure may be referred to as KYPHOCUBE. In an illustrative example such a balloon kyphoplasty surgical device allows for more surface area and different ways to lift the vertebra to fix a fracture. Such a balloon in accordance with the teaching of the present disclosure also allows for different orientations to inflate since it is not symmetrical, giving the doctor more abilities to lift the fracture in any way necessary.

Exemplary balloon kyphoplasty surgical device 10 implementations in accordance with the present disclosure are not limited to the number or shapes of balloons. The outer balloon may be sealed off but may have some form of lubrication inside the outer balloon, to reduce friction between the inner balloons. The sealed outer balloon may comprise lubrication retained within the sealed outer balloon. The sealed outer balloon may be manufactured having lubrication retained within the sealed outer balloon. The outer balloon will also assist in cushioning the inner balloons as they press on the bone.

In one embodiment, the inflated balloon arrangement 30 is in place for 5 seconds to 30 minutes.

In one embodiment, the inflated balloon arrangement 30 is inserted with a 10*f* or 11*f* access needle or trocar that varies in length and size. The access needle or trocar are placed in the vertebral body and allows the balloon arrangement 30 to enter through the needle or the trocar into the vertebrae. The access needle and trocar are not shown.

In sum, the balloon kyphoplasty surgical device may be made up of multiple balloons, an extrusion tube, support wire, and a multichambered proximal port. The multiple balloons may be positioned as inner and outer balloons to produce a cubic shape when inflated. The one or more larger outer balloon may be manufactured to be cubic in shape, while the inner balloons have a standard cylindrical/spherical shape and support the corners to maintain the square geometry under pressure. The extrusion tube comprises multiple fluid channels so that the inner and outer balloons can be inflated at different volumes. The support wire will ensure the device does not get damaged while inserting into the vertebra. The multichambered proximal port may comprise multiple ports that attach to separate chambers. These chambers connect to different fluid routes keeping the inlets separate, this separation will allow for independent filling during use.

The goal of balloon kyphoplasty surgical device is to achieve lift with a cubic like balloon shape. The various components described herein achieve this shape. After insertion the inner and outer balloons are inflated, the inner balloons are inflated to the size needed for the appropriate distance of lift. The outer balloon will have a volume of fluid added to produce the cubic shape. The inflation is done using the multichambered ports and separate inflation device reservoirs to maintain the appropriate pressure/volume needed. The balloon material must be noncompliant enough to undergo a minimum of 400 PSI without losing the cubic shape or bursting while still being compliant enough to stretch to the appropriate size.

The predicate kyphoplastic balloons operate in a similar fashion but use a standard circular balloon. The circular cavity created has proven to work but the cement structure formed after use can have high single point pressure areas that can weaken the bone at these points, these devices can also not allow for enough bone cement to be added for proper support. The balloon kyphoplasty surgical device creates a larger boney void or cavity with a larger flat surface area producing a more structurally sound structure after cementation. During compression of vertebra the bone is grown to exert this force through flat surfaces, and the cubic cement structure allows for a flat surface for the bone to compress on and for more cement to be packed in.

In an illustrative example, various implementations in accordance with the present disclosure may relate generally to medical devices, and more specifically to a balloon angioplasty device that may be referred to as ANGIOCUBE. Angioplasty is a minimally invasive procedure done to widen narrowed or obstructed blood vessels. The procedure accesses a blood vessel via a catheter inserted through an incision in the skin. Angioplasty is typically used to treat atherosclerosis caused by the buildup of plaque in a blood vessel but can also treat other conditions associated with narrowing or blockage of a blood vessel.

In an aspect, an exemplary implementation in accordance with the present disclosure may feature a balloon angioplasty surgical device including an extrusion tube having internal fluid channels and a guidewire channel, a port arrangement positioned on a proximal end (Y connector/ Injection Ports) of the extrusion tube and a balloon arrangement positioned on a distal end of the extrusion tube, the balloon arrangement resulting in a polygon shape when inflated by the port arrangement. The inner balloons may be housed inside of the outer balloons and each balloon may be inflated separately at the least or some balloons may be paired up and inflated separately by group. The outer balloon may be sealed. The separate inflation is possible due to the proximal injection ports having separate chambers to allow for the balloons to inflate independently. The device is used for opening narrowed or obstructed blood vessels. The outer balloon may be pressurized first and the inner balloons may be pressurized separately based on the needs of the patient's artery. This allows for weaker areas of the vessels to not receive as much pressure.

In an aspect, an implementation in accordance with the present disclosure may feature a balloon angioplasty surgical device including an extrusion tube having internal fluid channels and guidewire channel, a balloon arrangement positioned on a distal end of the extrusion tube, the balloon arrangement resulting in a polygon shape when inflated by the port arrangement, and wherein there are three or more inner balloons. The inner balloons may be housed inside of the outer balloons, each balloon may be inflated separately at the least, some balloons may be paired up and inflated separately by group or inflated all together. The separate inflation of the individual balloons is possible due to the proximal injection ports having separate chambers to allow for the individual balloons to inflate independently. The proximal Y connection/Injection Ports section may have at least two or more injection ports. One injection port may be configured for the guidewire channel, one injection port may be configured for the outer balloon, and other injection ports may be configured for the inner balloon. The device may be used for opening narrowed or obstructed blood vessels. The outer balloon may be pressurized first and the inner balloons may be pressurized separately based on the needs of the patient's artery. This allows for weaker areas of the vessels to not receive as much pressure. Prior technologies inflate a circular balloon across the entire area of the artery, some can inflate at different pressures axially but none of the existing technologies can inflate the arteries cross sectional area separately.

Various angioplasty balloon catheter implementations in accordance with teachings of the present disclosure may advantageously increase successful procedures and allow for limiting arterial damage as a result of an angioplasty balloon catheter designed to permit radial forces applied to the cross-sectional area of the artery to be customized based on the patient's needs. This facilitation may be a result of the use of inner balloons, individual fluid chambers that can inflate all the inner balloons separately or in groups or all together, a fluid chamber that can inflate the outer chamber, and a device configured to form an exemplary Polygon shape using inner and outer balloons (for example, a shape close to a circle formation but having some edges due to inner balloons).

Some exemplary AngioCube implementations in accordance with the teachings of the present disclosure may be configured with a various number of inner balloons and the inner balloons' internal configuration, size, and number may vary. Some examples may comprise more than three inner balloons. The number of ports may be greater than two, to allow for individual filling of inner balloons if needed. (For example, 6 balloons may be configured to be individually filled and include a guidewire port resulting in a design having 7 ports, or 6 balloons may be configured in groups of two filled separately and include a guidewire port resulting in a design having 4 ports). An implementation in accordance with the present disclosure may be configured with an Injection Port and Y connector designed to be separate or a combined entity. In some implementations the materials of the guidewire and extrusion tube may be interchanged. An exemplary AngioCube implementation in accordance with the present disclosure may be designed for inflation across the entire volume of the outer balloon and may be permanently installed in the outer balloon, and may also advantageously exert radial force differently across the cross sectional area of the artery, in contrast with some prior art devices that insert an inner balloon during the operation and disadvantageously inflate a smaller volume than the outer balloon while exerting equal force in all radial directions.

An exemplary kyphoplasty surgical method may comprise placing an extrusion tube through an incision in a patient, wherein the extrusion tube is operably coupled with a kyphoplasty balloon arrangement located at one end of the extrusion tube, and wherein the kyphoplasty balloon arrangement comprises a plurality of inner balloons retained within an outer balloon, and wherein the outer balloon is configured to be separately inflatable from the plurality of inner balloons, wherein each inner balloon and the outer balloon are in fluid communication with a single fluid channel thereby forming independently inflatable balloons.

The kyphoplasty surgical method may further comprise pushing the extrusion tube along a path through a pedicle of an involved vertebra and into a fractured area.

The kyphoplasty surgical method may further comprise positioning the kyphoplasty balloon arrangement to align the balloon arrangement with at least one involved vertebra.

The kyphoplasty surgical method may further comprise inflating the balloon arrangement.

The kyphoplasty surgical method may further comprise placing the patient on a table face down.

The kyphoplasty surgical method may further comprise making the incision in the patient's back.

The kyphoplasty surgical method may further comprise cleaning the patient's back.

The kyphoplasty surgical method may further comprise administering anesthesia to the patient.

The kyphoplasty surgical method may further comprise deflating and removing the balloon arrangement to form a cavity.

The kyphoplasty surgical method may further comprise filling the cavity with a cement-like material; and allowing the cement-like material to harden.

Each inner balloon of the plurality of inner balloons may be manufactured to produce an inner balloon predetermined shape upon inflation.

The inner balloon predetermined shape may further comprise a spherical shape.

The inner balloon predetermined shape may further comprise a cylindrical shape.

The outer balloon may be manufactured to produce a predetermined shape upon outer balloon inflation.

The outer balloon predetermined shape may be cubic.

Align the balloon arrangement may further comprise aligning a top surface and a bottom surface of at least one balloon relative to at least one involved vertebra.

Align the balloon arrangement may further comprise aligning a top surface and a bottom surface of at least one inner balloon to be parallel with at least one involved vertebra.

Align the balloon arrangement may further comprise aligning a top and a bottom surface of at least one inner balloon to be square to a respective involved vertebrae.

Inflating the balloon arrangement may further comprise inflating at least one inner balloon after positioning the balloon arrangement to align the at least one inner balloon with at least one involved vertebra.

Inflating the balloon arrangement may further comprise inflating the outer balloon after inflating at least one inner balloon.

An exemplary kyphoplasty surgical method may comprise placing an extrusion tube through an incision in a patient's back, wherein the extrusion tube comprises at least two internal fluid channels and a support wire and the at least two internal fluid channels are configured to be in fluid communication with a port arrangement positioned on a proximal end of the extrusion tube, wherein a distal end of the extrusion tube is configured with a balloon arrangement configured to be in fluid communication with the at least two internal fluid channels, the balloon arrangement resulting in a cubic shape when inflated thereby forming six flat surfaces, and wherein the balloon arrangement comprises a plurality of inner balloons housed within an outer balloon; wherein the inner balloons are configured to be in fluid communication with a single fluid channel and the outer balloon is configured to be in fluid communication with a single fluid channel thereby forming independently inflatable inner and outer balloons, wherein each inner balloon of the plurality of inner balloons is configured to be in fluid communication with a respective port/channel for each inner balloon.

The kyphoplasty surgical method may further comprise making the incision in the patient's back.

The kyphoplasty surgical method may further comprise pushing the extrusion tube along a path through a pedicle of an involved vertebra and into a fractured area.

The kyphoplasty surgical method may further comprise positioning the kyphoplasty balloon arrangement to align the balloon arrangement with at least one involved vertebra.

At least one inner balloon may have a cylindrical shape.

At least one inner balloon may have a spherical shape.

The plurality of inner balloons may be at least four inner balloons.

The plurality of inner balloons may be at least two inner balloons.

Each inner balloon of the plurality of inner balloons may be in fluid communication with the respective port/channel.

The at least two internal fluid channels may be in fluid communication with the port arrangement and the balloon arrangement.

An exemplary apparatus may comprise an extrusion tube comprising at least three internal fluid channels and a support wire; a port arrangement positioned on a proximal end of the extrusion tube in fluid communication with the at least three internal fluid channels; and a balloon arrangement positioned on a distal end of the extrusion tube in fluid communication with the at least three internal fluid channels, the balloon arrangement resulting in a cubic shape when inflated, wherein the balloon arrangement comprises a plurality of inner balloons housed within an outer balloon; wherein each inner balloon and the outer balloon are in fluid communication with a single fluid channel thereby forming independently inflatable balloons.

Each of the plurality of inner balloons may be manufactured to produce an inner balloon predetermined shape upon inflation.

The inner balloon predetermined shape may further comprise a spherical shape.

The inner balloon predetermined shape may further comprise a cylindrical shape.

The outer balloon may be manufactured to produce a cubic shape upon inflation.

The port arrangement may comprise at least three ports in fluid communication with the at least three internal fluid channels and in fluid communication with at least one inflation device reservoir.

At least two of the at least three ports may be configured to inflate the plurality of inner balloons and one of the at least three ports is configured to inflate the outer balloon.

An exemplary apparatus may comprise a plurality of inner balloons retained within an outer balloon, wherein the outer balloon is configured to be separately inflatable from the plurality of inner balloons, and wherein each inner balloon and the outer balloon are in fluid communication with a single fluid channel thereby forming independently inflatable balloons.

The outer balloon may be sealed.

The outer balloon may be manufactured as a sealed outer balloon.

Each inner balloon of the plurality of inner balloons may be manufactured to produce a predetermined inner balloon shape upon inflation.

The predetermined inner balloon shape may further comprise a spherical shape.

The predetermined inner balloon shape may further comprise a cylindrical shape.

The plurality of inner balloons may be at least four inner balloons.

The plurality of inner balloons may be at least two inner balloons.

The outer balloon may be manufactured to produce a cubic shape upon inflation.

Ane exemplary apparatus may comprise an extrusion tube comprising at least two internal fluid channels and a support wire; a port arrangement positioned on a proximal end of the extrusion tube in fluid communication with the at least two internal fluid channels; and a balloon arrangement positioned on a distal end of the extrusion tube in fluid communication with the at least two internal fluid channels, the balloon arrangement resulting in a cubic shape when inflated thereby forming six flat surfaces, wherein the balloon arrangement comprises a plurality of inner balloons housed within an outer balloon; wherein the inner balloons are configured to be in fluid communication with a single fluid channel and the outer balloon is configured to be in fluid communication with a single fluid channel thereby forming independently inflatable inner and outer balloons; wherein each inner balloon of the plurality of inner balloons is configured to be in fluid communication with a respective port/channel for each inner balloon.

At least one inner balloon may have a cylindrical shape.

At least one inner balloon may have a spherical shape.

The plurality of inner balloons may be at least four inner balloons.

The plurality of inner balloons may be at least two inner balloons.

Each inner balloon of the plurality of balloons may be configured to be in fluid communication with a respective port/channel for each inner balloon.

An exemplary apparatus may comprise an extrusion tube comprising at least two internal fluid channels and a support wire; a port arrangement positioned on a proximal end of the extrusion tube in fluid communication with the at least two internal fluid channels; and a balloon arrangement positioned on a distal end of the extrusion tube in fluid communication with the at least two internal fluid channels, the balloon arrangement resulting in a cubic shape when inflated, wherein the balloon arrangement comprises a plurality of inner balloons housed within a sealed outer balloon; wherein each inner balloon is in fluid communication with a single fluid channel thereby forming independently inflatable inner balloons.

The sealed outer balloon may retain lubrication.

The port arrangement may comprise at least two ports in fluid communication with the at least two internal fluid channels and in fluid communication with at least one inflation device reservoir.

The at least two ports may be configured to inflate the plurality of inner balloons.

An exemplary apparatus may comprise a plurality of inner balloons retained within a sealed outer balloon, wherein each inner balloon is in fluid communication with a single fluid channel thereby forming independently inflatable inner balloons.

The sealed outer balloon may be manufactured with a plurality of corners disposed to constrain the plurality of inner balloons to a cubic-like shape when individual inner balloons are independently inflated.

An exemplary apparatus may comprise an extrusion tube comprising at least two internal fluid channels and a support wire; a port arrangement positioned on a proximal end of the extrusion tube in fluid communication with the at least two internal fluid channels; and a balloon arrangement positioned on a distal end of the extrusion tube in fluid communication with the at least two internal fluid channels, the balloon arrangement resulting in a cubic shape when inflated thereby forming six flat surfaces, wherein the balloon arrangement comprises a plurality of inner balloons housed within a sealed outer balloon retaining lubrication, wherein the sealed outer balloon is manufactured with a plurality of corners; wherein the inner balloons are configured to be in fluid communication with a single fluid channel thereby forming independently inflatable inner balloons; wherein each inner balloon of the plurality of inner balloons is configured to be in fluid communication with a respective port/channel for each inner balloon.

While various embodiments of the present disclosure have been described above, it should be understood that they have been presented by way of example only, and not of limitation. Likewise, the various diagrams may depict an example architectural or other configuration for the present disclosure, which is provided to aid in understanding the features and functionality that may be included in an exemplary implementation in accordance with the present disclosure. An exemplary implementation in accordance with the present disclosure is not restricted to the illustrated example architectures or configurations, but the desired features can be implemented using a variety of alternative architectures and configurations.

Indeed, it will be apparent to one of skill in the art how alternative functional configurations can be implemented to implement the desired features of the present disclosure. Additionally, with regard to flow diagrams, operational descriptions and method claims, the order in which the steps are presented herein shall not mandate those various embodiments be implemented to perform the recited functionality in the same order unless the context dictates otherwise.

In the present disclosure, various features may be described as being optional, for example, through the use of the verb "may;" or, through the use of any of the phrases: "in some implementations," "in some designs," "in various implementations," "in various designs," "in an illustrative example," or, "for example." For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be implemented in seven different ways, namely with just one of the three possible features, with any two of the three possible features or with all three of the three possible features.

The phrases "connected to," "coupled to" and "in communication with" refer to any form of interaction between two or more entities, including mechanical, electrical, magnetic, electromagnetic, fluid, and thermal interaction. Two or more components may be functionally coupled to each other even though they are not in direct contact with each other. The terms "abutting" or "in mechanical union" may refer to items that are in direct physical contact with each other, although the items may not necessarily be attached together. In various implementations, elements described herein as coupled or connected may have an effectual relationship realizable by a direct connection or indirectly with one or more other intervening elements.

Recitation in a claim of the term "first" with respect to a feature or element does not necessarily imply the existence of a second or additional such feature or element.

Although the disclosure is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosure, whether or not such embodiments are described and whether or not such features are presented as being a part of a described embodiment. Thus, the breadth and scope of the present invention should not be limited by any of the above-described exemplary embodiments.

What is claimed is:

1. A balloon kyphoplasty surgical device comprising:
an extrusion tube comprising at least two internal fluid channels and a support wire;
a port arrangement positioned on a proximal end of the extrusion tube in fluid communication with the at least two internal fluid channels; and
a balloon arrangement positioned on a distal end of the extrusion tube in fluid communication with the at least two internal fluid channels, the balloon arrangement resulting in a cubic shape when inflated, wherein the balloon arrangement comprises a plurality of inner balloons housed within a sealed outer balloon; wherein each inner balloon is in fluid communication with a respective internal fluid channel of the at least two internal fluid channels thereby forming independently inflatable inner balloons; and wherein the sealed outer balloon is configured to conform around the inner balloons as they inflate, creating a cubic shape, and the sealed outer balloon is manufactured having lubrication retained within the sealed outer balloon.

2. The balloon kyphoplasty surgical device of claim 1, wherein each of the plurality of inner balloons is manufactured to produce an inner balloon predetermined shape upon inflation.

3. The balloon kyphoplasty surgical device of claim 2, wherein the inner balloon predetermined shape further comprises a spherical shape.

4. The balloon kyphoplasty surgical device of claim 2, wherein the inner balloon predetermined shape further comprises a cylindrical shape.

5. The balloon kyphoplasty surgical device of claim 1, wherein the port arrangement comprises at least two ports in fluid communication with the at least two internal fluid channels and in fluid communication with at least one inflation device reservoir.

6. The balloon kyphoplasty surgical device of claim 5, wherein the at least two ports are configured to inflate the plurality of inner balloons.

7. A kyphoplasty balloon arrangement comprising: a plurality of inner balloons retained within a sealed outer balloon, wherein each inner balloon is in fluid communication with a respective fluid channel of a plurality of fluid channels thereby forming independently inflatable inner balloons, and wherein the sealed outer balloon is configured to conform around the inner balloons as they inflate, creating a cubic shape, and the sealed outer balloon is manufactured having lubrication retained within the sealed outer balloon.

8. The kyphoplasty balloon arrangement of claim 7, wherein each inner balloon of the plurality of inner balloons is manufactured to produce a predetermined inner balloon shape upon inflation.

9. The kyphoplasty balloon arrangement of claim 8, wherein the predetermined inner balloon shape further comprises a spherical shape.

10. The kyphoplasty balloon arrangement of claim 8, wherein the predetermined inner balloon shape further comprises a cylindrical shape.

11. The kyphoplasty balloon arrangement of claim 7, wherein the plurality of inner balloons is at least four inner balloons.

12. The kyphoplasty balloon arrangement of claim 7, wherein the plurality of inner balloons is at least two inner balloons.

13. The kyphoplasty balloon arrangement of claim 7, wherein the sealed outer balloon is manufactured with a plurality of corners disposed to constrain the plurality of inner balloons to a cubic-like shape when individual inner balloons are independently inflated.

14. A balloon kyphoplasty surgical device comprising:
an extrusion tube comprising at least two internal fluid channels and a support wire;
a port arrangement positioned on a proximal end of the extrusion tube in fluid communication with the at least two internal fluid channels; and
a balloon arrangement positioned on a distal end of the extrusion tube in fluid communication with the at least two internal fluid channels, wherein the balloon arrangement comprises a plurality of inner balloons housed within a sealed outer balloon retaining lubrication; wherein each inner balloon of the plurality of inner balloons is configured to be in fluid communication with a respective internal fluid channel of the at least two internal channels thereby forming independently inflatable inner balloons, and wherein the sealed outer balloon is configured to conform around the inner balloons as they inflate, creating a cubic shape, and the sealed outer balloon is manufactured having lubrication retained within the sealed outer balloon.

15. The balloon kyphoplasty surgical device of claim 14, wherein at least one inner balloon has a cylindrical shape.

16. The balloon kyphoplasty surgical device of claim 14, wherein at least one inner balloon has a spherical shape.

17. The balloon kyphoplasty surgical device of claim 14, wherein the plurality of inner balloons is at least four inner balloons.

18. The balloon kyphoplasty surgical device of claim 14, wherein the sealed outer balloon is manufactured with a plurality of corners, and wherein the balloon arrangement results in a cubic shape when inflated thereby forming six substantially flat surfaces.

* * * * *